United States Patent

Porter et al.

Patent Number: 5,591,199
Date of Patent: Jan. 7, 1997

[54] CURABLE FIBER COMPOSITE STENT AND DELIVERY SYSTEM

[76] Inventors: Christopher H. Porter, 19756 NE. 127th Pl., Woodinville, Wash. 98072; Robert Van Tassel, 6420 Bayview Pl., Excelsior, Minn. 55331; Curtis Amplatz, 546 N. Lexington Pky., St. Paul, Minn. 55104; Michael Kasinkas, 11700 26th Ave. N., Plymouth, Minn. 55441

[21] Appl. No.: 477,759

[22] Filed: Jun. 7, 1995

[51] Int. Cl.[6] .................................................. A61M 29/00
[52] U.S. Cl. ........................ 606/198; 606/194; 606/192; 623/1; 623/12
[58] Field of Search ........................... 606/194, 195, 606/192, 198, 191; 623/1, 12; 604/96, 194

[56] References Cited

U.S. PATENT DOCUMENTS

| | | | |
|---|---|---|---|
| 4,886,062 | 12/1989 | Wiktor | 128/343 |
| 4,902,290 | 2/1990 | Fleckenstein et al. | 623/1 |
| 5,061,275 | 10/1991 | Wallstén et al. | 623/1 |
| 5,092,841 | 3/1992 | Spears | 604/96 |
| 5,100,429 | 3/1992 | Sinofsky et al. | 606/195 |
| 5,147,385 | 9/1992 | Beck et al. | 623/1 |
| 5,163,951 | 11/1992 | Pinchuk et al. | 623/1 |
| 5,197,978 | 3/1993 | Hess | 623/1 |
| 5,213,580 | 5/1993 | Slepian et al. | 623/1 |
| 5,246,452 | 9/1993 | Sinnott | 623/1 |
| 5,282,846 | 2/1994 | Schmitt | 623/1 |
| 5,282,848 | 2/1994 | Schmitt | 623/1 |
| 5,295,962 | 3/1994 | Crocker et al. | 604/101 |
| 5,306,286 | 4/1994 | Stack et al. | 606/198 |
| 5,334,201 | 8/1994 | Cowan | 623/1 |
| 5,344,426 | 9/1994 | Lau et al. | 606/198 |
| 5,344,444 | 9/1994 | Glastra | 623/1 |
| 5,354,308 | 10/1994 | Simon et al. | 606/198 |
| 5,356,423 | 10/1994 | Tibon et al. | 606/194 |
| 5,366,504 | 11/1994 | Anderson et al. | 623/11 |
| 5,395,390 | 3/1995 | Simon et al. | 606/198 |
| 5,421,826 | 6/1995 | Crocker et al. | 606/194 |
| 5,443,495 | 8/1995 | Buscemi et al. | 623/1 |

*Primary Examiner*—Michael Powell Buiz
*Assistant Examiner*—Kevin Truong
*Attorney, Agent, or Firm*—Thomas J. Engellenner; Jane E. Remillard; Lahive & Cockfield

[57] ABSTRACT

A stent for supporting a selected portion of a body lumen, comprising a fibrous material which is treated with a curable material to form a curable fiber composite. The fiber composite is positioned within a body lumen and, upon curing of the curable material, forms a rigid support structure.

25 Claims, 3 Drawing Sheets

CURABLE FIBER COMPOSITE STENT AND DELIVERY SYSTEM

BACKGROUND OF THE INVENTION

The present invention relates to an endoluminal stent for supporting a selected region of a body lumen and to a method of forming and delivering the stent in situ.

Atherosclerosis is commonly treated by means of angioplasty through the use of a balloon catheter. Balloon angioplasty involves passing a small, balloon-tipped catheter percutaneously into an artery or vessel and up to the region of obstruction. The balloon is then inflated to dilate the area of obstruction. However, restenosis or reclosure of the blood vessel following angioplasty is a common occurrence. Factors contributing, at least in part, to restenosis include proliferation of smooth muscle cells in the stenosed region and recoil of the arterial or vessel wall. When luminal narrowing occurs, further coronary difficulties can be experienced, including strokes, arrhythmia, infarcts and even death.

One approach to the prevention of restenosis following angioplasty has been to insert a supportive stent into the treated area. This can be done using a conventional balloon catheter. In particular, the stent is placed over the balloon portion of the catheter in a contracted or collapsed position. The catheter is then inserted into a blood vessel adjacent to a stenosis, and the balloon is expanded so that the stent engages and supports the surrounding vessel wall.

Typically, endovascular stents are made of metals to provide the requisite strength for maintaining dilation of a stenosed blood vessel region. For example, U.S. Pat. No. 5,197,978 (Hess et al.) and U.S. Pat. No. 5,354,308 (Simon et al.) disclose thermally deformable stents made of nickel and titanium. U.S. Pat. No. 5,366,504 (Andersen et al.) discloses a stent made of loosely interlocked knitted loops containing metal wire.

Non-metallic stents have also been used for endovascular support. These devices are generally cylindrical structures made up of a sheet or sleeve of resilient, elastic material which can be cured or hardened following delivery of the stent to a selected region of a vessel. For example, U.S. Pat. No. 5,100,429 (Sinofsky) discloses an endovascular stent having a tubular body formed as a rolled sheet of a biologically compatible material having a cross-linkable adhesive material between overlapping portions of the rolled sheet. U.S. Pat. No. 5,344,201 (Cowan et al.) discloses an endovascular stent made up of an expandable sleeve containing a cross-linkable material which can be cured by exposure to radiation, and a film of biologically compatible material which encapsulates the sleeve. U.S. Pat. No. 5,344,444 (Glastra et al.) discloses a hollow expandable stent in the form of a ring, cylinder or sleeve containing a curable material. U.S. Pat. No. 5,344,426 (Lau et al.) and U.S. Pat. No. 5,306,286 (Stack et al.) disclose stents made of a flat sheet of material which is rolled up to form a cylinder and having a plurality of apertures. U.S. Pat. No. 5,282,848 (Schmitt et al.) discloses a self-supporting stent having a continuous uniform surface made up of a woven synthetic material.

Many prior art stent designs suffer from the disadvantage of having a relatively large diameter in their non-deployed state, making them difficult to deliver and presenting the risk of causing undue trauma to the vessel Additionally, prior art stents can be somewhat inflexible so that they fail to closely conform to the surrounding vessel wall when in place. Moreover, these stents often become a permanent pan of the body and do not allow for significant tissue in-growth or exposure of the lumen wall to circulating blood when in place.

It is therefore an object of the present invention to provide a transformable stent for supporting and reinforcing a body lumen which is very flexible in its preformed state and tightly engages the surrounding lumen wall when expanded into place. It is also an object of the present invention to provide a stent which has a very low profile, so that it is easy to deliver and does not block a large portion of the lumen flow channel. It is a further object of the present invention to provide a stent which, following its delivery into a selected region of a body lumen, is extremely strong so as to effectively support and strengthen the surrounding lumen wall, yet which allows significant exposure of the supported lumen wall to circulating blood. It is still a further object of the invention to provide a polymer-based stent which is bio-resorbable and can be impregnated with a controlled release drug.

SUMMARY OF THE INVENTION

According to the present invention, these and other objects and advantages are achieved by a curable fiber composite stent which, upon formation in situ inside a selected region of a body lumen, serves to support the lumen without significant obstruction to blood flow. The stent is made up of a biocompatible fibrous material which is coated, impregnated, filled, or otherwise treated with a curable material so that the fiber composite can be suitably shaped to support a portion of a body lumen and then cured to maintain the shape. In one embodiment of the invention, the fiber composite and the curable material are bioresorbable so that the stent does not become a permanent part of the body.

The stent has an open, non-continuous structure, allowing for significant exposure of the lumen wall to circulating blood and for endothelial overgrowth. In one embodiment of the invention, the stent has a helical conformation. In another embodiment, the stent comprises a number of fibrous strands which are braided to form a porous mesh. The fibrous strands are treated with a curable material, for example, by saturating the strands with a photoactivatable cross-linking agent. Alternatively, the strands can be hollow fibers which are filled with a curable material. The fiber composite can then be coated with a film of a biocompatible material which insulates the curable material-containing fiber composite from the lumen wall and circulating blood. Alternatively, the curable material can be microencapsulated and then contacted with the fibrous material, thereby forming a biocompatible curable fiber composite.

To deliver the fiber composite stent to a selected region of a body lumen, the stent is mounted on the head of a deflated balloon catheter while in a flexible, non-cured state, guided into place, and then expanded by inflation of the balloon so that the stent tightly presses against the surrounding lumen wall. The stent is then cured so that it forms a rigid support structure which closely conforms to the lumen wall. In a preferred embodiment of the invention, the curing is achieved by exposure of the stent to UV light which is delivered through the balloon via a fiber optic tip. Following curing of the stent, the balloon is deflated and removed, leaving behind a rigid stent.

The curable fiber composite stent of the invention can be used to widen and support any body lumen, including, but not limited to vascular, urological, biliary, esophageal, reproductive, endobronchial, gastrointestinal, and prostatic lumens. The stent can also be used to deliver therapeutic agents to cells of a lumen wall. In one embodiment of the invention, the therapeutic agent is incorporated into the stent so that it is pressed into the surrounding lumen wall upon expansion of the stent. In another embodiment of the invention, the therapeutic agent is photoreleasably linked to the surface of the stent so that, upon exposure to light, the agent is released from the stent surface onto the surrounding lumen wall. The stent of the invention can also be used to treat acute vascular occlusion, dissection of an artery, or sub-optimal angioplasty.

The present invention provides the advantage of an endovascular stent which has a relatively low profile so that it can be easily guided through a body lumen and does not substantially obstruct blood or air flow when in place. The stent is also very flexible upon delivery so that it tightly conforms to the surrounding wall when expanded into place. Once formed in place, the stent is strong so that it supports and strengthens the lumen wall.

BRIEF DESCRIPTION OF THE DRAWINGS

FIG. 3 (c) shows the braided stent in a fully cured state, supporting the lumen wall.

DETAILED DESCRIPTION OF THE INVENTION

In accordance with one embodiment of the present invention shown in FIGS. 1 (a) and 1 (b), there is provided a stent 4 for supporting a selected region of a body lumen 7. The stent consists of a fibrous material which is treated with a curable material and then formed into a helix which engages the surrounding lumen wall 7. The stent is formed in situ, for example, within a stenosed region of a blood vessel, thereby reducing the risk of injury to the vessel wall resulting from delivery of a preformed stent.

Figure 2:
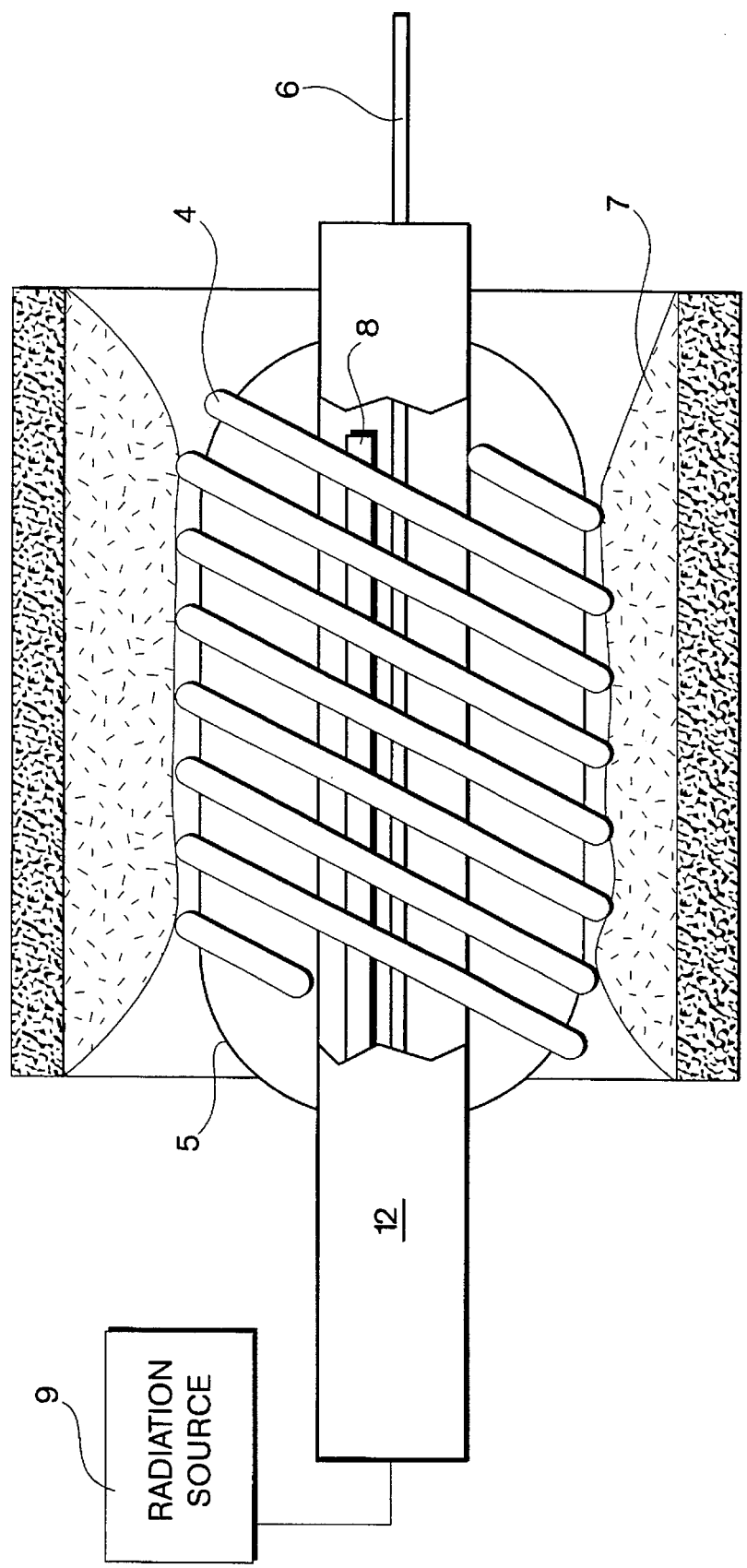
FIG. 2 shows how the stent of FIGS. 1(a) and 1(b) is positioned within a stenosed region of a lumen, expanded on the head of a balloon catheter, and irradiated to effect curing.

The stent 4 is formed and delivered using a conventional balloon catheter, as shown in FIG. 2. Such catheters are well known in the art and generally include an elongated flexible tube 12 with an expandable balloon 5 attached at the distal end. The catheter also includes at least one optical fiber 8 for delivering radiation into the balloon 5. At its proximal end, the optical fiber is connected to a source of radiation 9, such as a laser. Suitable lasers for delivering radiation are described, for example, in U.S. Pat. application Ser. No. 07/598,033 filed Oct. 10, 1990, now U.S. Pat. No. 5,175,663 the disclosure of which is incorporated by reference herein. The optical fiber 8 extends through the catheter body 12 into the balloon 5 attached to the distal end. The tip of the fiber is preferably designed to diffuse light outwardly through the balloon, for example, by tapering the end or by using a diffusive radio-opaque material, as is well known in the art.

Figure 1A:
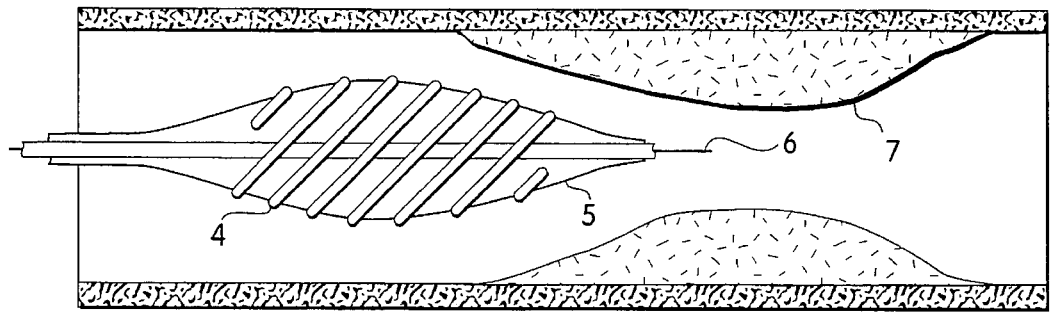
FIG. 1(a) shows a helical fiber composite stent coiled about a deflated balloon catheter, prior to being cured.
Figure 1B:
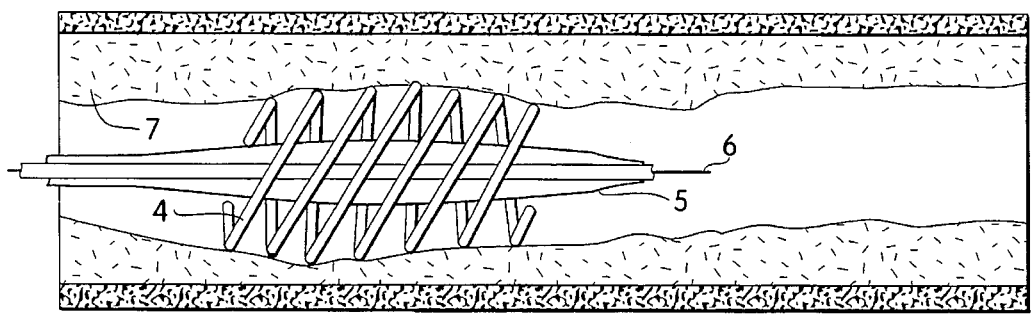
FIG. 1(b) shows the helical stent in a fully cured state, positioned within a stenosed lumen.

To form and deliver stent 4, a fibrous strand can be saturated or otherwise treated with a curable material, thereby forming a curable fiber composite. The fiber composite is then coiled about a cylindrical mandrel or similar device to form a helix. The helical fiber composite is then mounted over the head of a deflated balloon catheter 5, as shown in FIG. 1(a), prior to being cured. The catheter is then advanced using guidewire 6 through a body lumen to selected area 7, such as an obstructed blood vessel. Once adjacent to the region, the balloon 5 is expanded, so that the flexible stent is pressed tightly against the surrounding lumen wall 7, as shown in FIG. 2. Radiation is then delivered into the balloon via the optical fiber(s) 8 or other energy conducting means, causing the curable material in the stent to cross-link or polymerize and form a rigid support structure which closely conforms to the surrounding lumen wall 7, as shown in FIG. 1(b). The balloon is then deflated and the catheter is removed.

In another embodiment of the invention, the stent is made up of a hollow fiber, such as a polyethylene terephthalate (PET) tube, which encapsulates a curable material. The filled fiber tubing can be mounted on a balloon catheter and delivered to a selected region of a body lumen as described in the first embodiment of the invention. However, because the curable material is encapsulated by the fiber composite, the risk of toxicity from the curable material is largely reduced.

Figure 3A:
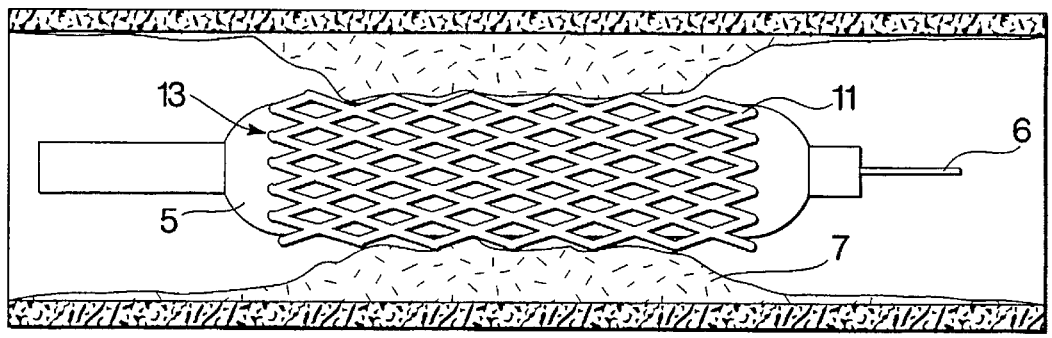
FIG. 3(a) shows a braided fiber composite stent placed lengthwise over the head of a deflated balloon catheter and positioned within a stenosed region of a body lumen.
Figure 3B:
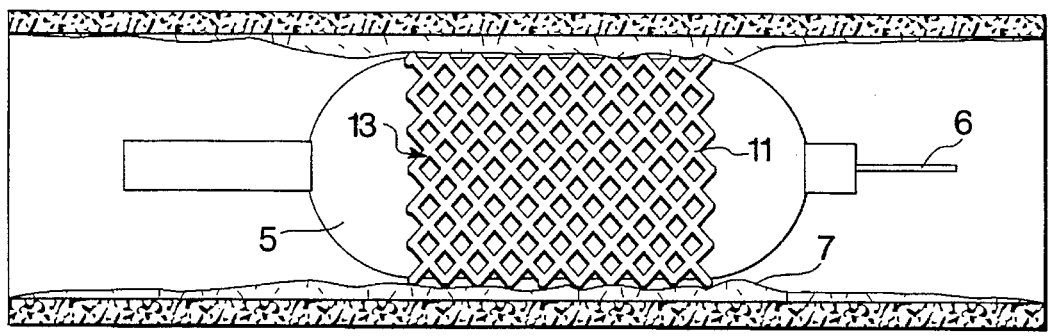
FIG. 3 (b) shows the braided stent in an expanded state, following inflation of the balloon.
Figure 3C:
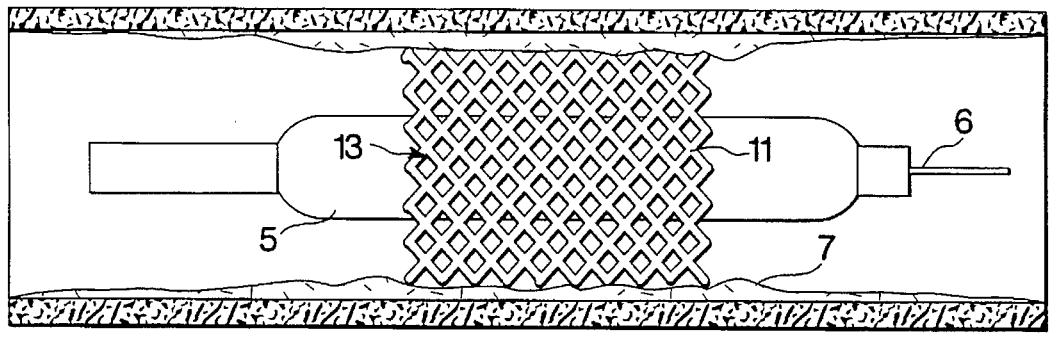

In yet another embodiment of the invention shown in FIGS. 3(a), (b), and (c), the stent 13 is made up of a number of fibrous strands 11 which are braided to form a porous mesh. In one example, approximately 16 strands of a fiber composite such as polyethylene terephthalate (Dacron), silk, or carbon are braided and then saturated with a UV curable material. To deliver stent 13 to a selected region of a body lumen, the flexible braid is pulled lengthwise over a deflated balloon catheter 5, as shown in FIG. 3(a). The stent is then guided through the lumen to the target site and expanded via balloon 5, as previously described in the first embodiment of the invention. Following expansion of the balloon, radiation is delivered into its interior via optical fiber 8, causing the braid to be cured while taking shape of the surrounding lumen wall 7, as shown in FIG. 3(b). Exposure to the light causes the curable material in contact with the fibers of the braid to stiffen the braid, resulting in a rigid, open mesh stent as shown in FIG. 3(c).

Fibrous materials suitable for use in the stent of the present invention include a variety of multi-filament fabrics and hollow fibers. The term "fibrous material", as used herein, encompasses all such fabrics and fibers including, for example, cotton, polyester, polyethylene terephthalate (Dacron), carbon and metal. The fibers making up the composite have a very small diameter and can freely move over one another, thereby providing flexibility when in an uncured state. However, upon bonding the fibers with a curable material by, for example, exposure to UV radiation, the fibers form a very strong, rigid support structure.

The fiber composite is formed into a rigid support structure by bonding the fibers with a material which can be cured by, for example, exposure to radiation, such as urethanes, polyurethane oligomer mixtures, acrylate monomers, aliphatic urethane acrylate oligomers, acrylamides, UV curable epoxies, and other UV curable monomers. Alternatively, the curable material can be a material capable of being chemically cured, such as silicone-based compounds which undergo room temperature vulcanization (RTV). Materials which harden over time can also be used, such as epoxies. The term "curable material", as used herein, is intended to include any material capable of being cross-linked or polymerized. In one embodiment, a UV curable polyurethane oligomer mixture, such as Dymax™ (available from Dymax Corp., Torrington, Conn.) is used and cross-linked using a Dymax™ UV curing machine, model PC-3. In another embodiment, UV polymerizable mixture of acrylate monomers, aliphatic urethane acrylate oligomers, and acrylamides, such as Loctite™ 3301 (available from Loctite Corp., Newington, Conn.) is used.

When using materials which are cured by exposure to radiation, the type and duration of radiation will vary according to the particular material used. While UV radiation is preferred, visible, infrared and thermal radiation can also be used to promote cross-linking of the fibers making up the stent. In a preferred embodiment of the invention, UV radiation having a wavelength ranging from 240–400 nm, is used which is provided by, for example, a non-coherent UV light source or an excimer source, such as a KrF excimer laser operating at 248 nanometers. Alternatively, a frequency-quadrupled, solid state, Neodymium-doped YAG laser or the like operating at 266 nm can be used, or an Argon ion laser operating at 257 or 275 or 360 nm can be used.

To reduce the risk of toxicity from the curable material prior to curing, the stent can further include a layer of a biocompatible material which encapsulates the curable fiber composite and serves as a barrier between the stent and any circulating blood, and between the stent and the lumen wall. Suitable biocompatible materials which can be used for this purpose include, but are not limited to, silicones, waxes, polyacrylamides, polyethylenes, polystyrenes, polypropylenes, polyolefins, polyurethanes and other thermoplastic elastic polymers. In one embodiment of the invention, a multi filament fiber (e.g., cotton or carbon) is saturated with UV curable material and then encapsulated within a polyethylene terephthalate (PET) shrink tubing.

The stent can also include a therapeutic agent which is incorporated into the fiber matrix of the stent, or into the biocompatible coating which encapsulates the stent, so that it can be released onto the cells of the surrounding lumen wall upon expansion and curing of the stent within a body lumen. For example, the therapeutic agent can be impregnated into the lumen wall by pressure tom expansion of the stent. Alternatively, the therapeutic agent can be photoreleasably linked to the surface of the stent so that, upon contact with the surrounding lumen wall, the agent is released onto the cells of the wall by exposure to radiation delivered via the optical fiber into the balloon.

Therapeutic agents which can be delivered via the stem of the invention include any agent or combination of agents that may affect the cells in the vessel wall, including drugs, chromophores, and nucleic acids. Therapeutic agents also include diagnostics which will aid in later treatment, such as radiopaque compounds that allow the vessel to be visualized by fluoroscopy or similar methods. Therapeutic agents may further include antimicrobial agents, such as antibacterial and antiviral agents.

For restenosis inhibition, it is typically desirable to arrest the proliferation of smooth muscle cells. Accordingly, drugs which prevent platelet aggregation and adhesion can be used, such as antiplatelets, antithrombogenics, and anticoagulants. In addition, receptor blockers, growth factors and other hormones may be used to limit the normal repair response. The following are groups of particular drugs which can be used to treat vascular disease, such as atherosclerosis and restenosis: anticoagulants, including heparin, hirudin, hirulog, tissue plasminogen activator, and fibrinogen; anti-inflammatory agents, such as steroids, ibuprofen, aspirin, somatostatin, angiopeptin, and anti-inflammatory peptide 2; cytotoxins, including colchicine, dexamethasone, doxorubicin, methotrexate, and psoralen; antibiotics; and enzymes and enzyme inhibitors, including urokinase, 2,4-dinitrophenol, and thiol protease inhibitor.

Another aspect of the present invention provides a curable fiber composite stent which is bioresorbable. For example, the fibrous component of the stent can be made of polyglycolic acid and other materials used in bioresorbable sutures. Due to the open, noncontinuous structure of the stent, which allows significant exposure of the lumen wall to circulating blood, the stent is encapsulated by endothelial tissue of the lumen wall by growth of the tissue over the fibers. The resulting layer of tissue further reinforces and supports the lumen. However, the stent will be absorbed before the encapsulating tissue thickens to an undesirable level.

Equivalents

Those skilled in the art will be able to recognize, or be able to ascertain using no more than routine experimentation, numerous equivalents to the specific compositions and procedures described herein. Such equivalents are considered to be within the scope of this invention and are covered by the following claims.

What is claimed is:

1. A stent for supporting a selected portion of a body lumen, comprising at least one flexible fiber composite which is formed to engage the wall of a body lumen, wherein the fiber composite comprises a plurality of fibers and a curable material in contact with the fibers, wherein said stent positioned within the body lumen and, upon curing of the curable material, the fibers are bonded together to form a rigid support structure.

2. The stent of claim 1, wherein the fibers are coated with the curable material.

3. The stent of claim 1, wherein the fiber composite comprises a hollow fiber which encapsulates the curable material.

4. The stent of claim 1, wherein the fiber composite is further contacted with a therapeutic agent.

5. The stent of claim 4, wherein the therapeutic agent is an antithrombogenic agent.

6. The stent of claim 1, wherein the fiber composite has a helical conformation.

7. The stent of claim 1, wherein the fiber composite comprises a plurality of strands which are braided to form a porous mesh.

8. The stent of claim 1, further comprising a layer of a biocompatible material which encapsulates the fiber composite.

9. The stent of claim 8, wherein the biocompatible material is selected from the group consisting of silicones, waxes, polyacrylamides, polyethylenes, polystyrenes, polypropylenes, polyolefins, and polyurethanes.

10. The stent of claim 8, wherein the biocompatible material further comprises a therapeutic agent.

11. The stent of claim 1, wherein the fiber composite is bioresorbable.

12. The stent of claim 1, wherein the fiber composite comprises a multifilament fabric selected from the group consisting of polyester, cotton, polyethylene terephthalate, and carbon.

13. The stent of claim 1, wherein the curable material is UV curable.

14. The stent of claim 13, wherein the curable material is selected from the group consisting of epoxies, silicones, urethanes, acrylamides, and polyurethane oligomer mixtures.

15. The stent of claim 1, wherein the curable material is thermally curable.

16. The stent of claim 1, wherein the curable material is chemically curable.

17. An apparatus for forming a stent inside a body lumen comprising:

a flexible elongated tube having a light transmitting expandable balloon attached to its distal end;

at least one fiber composite desposed about the expandable balloon, the fiber composite comprising a plurality of fibers and a curable material in contact with the fibers;

catheter means connected to said flexible tube and said balloon for inflating the balloon; and energy conducting means for transmitting radiation from an outside source to the interior of the balloon, the radiation being of a sufficient energy to cause curing of the curable material, thereby bonding together the fibers of the fiber composite, resulting in the formation of a rigid support structure.

18. The apparatus of claim 17, wherein the energy conducting means is an optical fiber.

19. The apparatus of claim 17, wherein the radiation is UV radiation.

20. A method of forming a stent, comprising the steps of:

applying a curable material to a plurality of fibers, thereby forming a curable fiber composite;

shaping the fiber composite into a form suitable for insertion inside a body lumen;

mounting the shaped fiber composite over an expandable member;

disposing the expandable member in an unexpanded state inside a body lumen;

locating the expandable member adjacent to a selected region of the body lumen;

inflating the expandable member so as to bring the fiber composite into contact with the surrounding lumen wall; and curing the curable material so as to bond together the fibers of the fiber composite, thereby forming a rigid support structure.

21. The method of claim 20, further comprising the step of coating the fiber composite with a biocompatible material.

22. The method of claim 20, further comprising the step of braiding the fiber composite to form a porous mesh.

23. The method of claim 20, further comprising the step of impregnating a therapeutic agent into the fiber composite.

24. The method of claim 20, wherein the step of curing the curable material comprises cross-linking or polymerizing the curable material by irradiation.

25. The method of claim 24, wherein the irradiation comprises UV radiation.

* * * * *